(12) United States Patent
Snape

(10) Patent No.: US 6,372,734 B1
(45) Date of Patent: Apr. 16, 2002

(54) CRYSTALLINE DIBENZOTHIAZEPINE DERIVATIVE AND ITS USE AS AN ANTIPSYCHOTIC AGENT

(75) Inventor: Evan William Snape, Bristol (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/463,452

(22) PCT Filed: Jul. 28, 1998

(86) PCT No.: PCT/GB98/02260

§ 371 Date: Jan. 27, 2000

§ 102(e) Date: Jan. 27, 2000

(87) PCT Pub. No.: WO99/06381

PCT Pub. Date: Feb. 11, 1999

(30) Foreign Application Priority Data

Aug. 1, 1997 (GB) .............................. 9716161

(51) Int. Cl.$^7$ ................... A61K 31/55; A61P 25/18; C07D 281/16
(52) U.S. Cl. ................... 514/211.13; 540/551
(58) Field of Search ................. 540/551; 514/211.13

(56) References Cited

U.S. PATENT DOCUMENTS 4,879,288 A * 11/1989 Warawa et al. ............. 514/211

FOREIGN PATENT DOCUMENTS

EP 0 240 228 A 10/1987
EP 0 282 236 9/1988

* cited by examiner

*Primary Examiner*—Brenda Coleman
(74) *Attorney, Agent, or Firm*—Pillsbury Winthrop LLP

(57) ABSTRACT

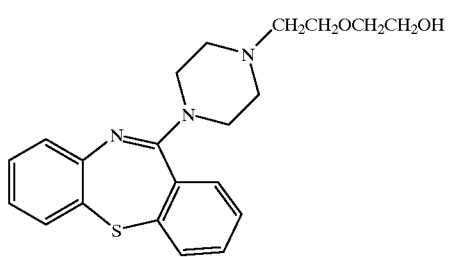

Crystalline 11-(4-[2-(2-hydroxyethoxy)ethyl]-1-piperazinyl)-dibenzo[b,f][1,4]thiazepine (I) may be prepared by crystallizing 11-(4-[2-(2-hydroxyethoxy)ethyl]-1-piperazinyl)-dibenzo[b,f][1,4]thiazepine from a non-aromatic solvent such as ethyl acetate, isobutyl acetate, methyl iso-butylketone or methyl tert-butyl ether, preferably in the absence of water. The crystalline material produced may be converted into a pharmaceutically acceptable salt such as a fumarate. The crystalline 11-(4-[2-(2-hydroxyethoxy)ethyl]-1-piperazinyl)-dibenzo[b,f][1,4]thiazepine may be used to treat psychoses.

22 Claims, No Drawings

CRYSTALLINE DIBENZOTHIAZEPINE DERIVATIVE AND ITS USE AS AN ANTIPSYCHOTIC AGENT

This application is the national phase under 35 U.S.C § 371 of international application PCT/GB98/2260, filed Jul. 28, 1998.

The present invention relates to a process for the preparation of thiazepine derivatives and, in particular, to the preparation of 11-(4-[2-(2-hydroxyethoxy)ethyl]-1-piperazinyl)-dibenzo[b,f][1,4]thiazepine and salts thereof.

The compound, 11-(4-[2-(2-hydroxyethoxy)ethyl]-1-piperazinyl)-dibenzo[b,f][1,4]thiazepine (Formula I)

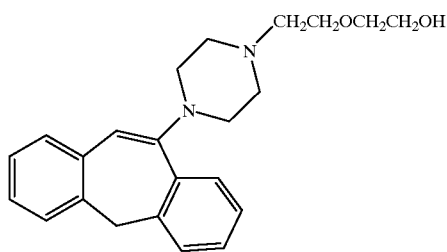

Formula I exhibits useful antidopaminergic activity and may be used, for example, as an antipsychotic agent with a substantial reduction in the potential to cause side effects such as acute dystonia, acute dyskinesia, pseudo-Parkinsonism and tardive dyskinesia.

The compound of formula I is described in granted European Patent EP 240,228. This patent describes the properties of the compound of formula I and its synthesis from dibenzo[b,f][1,4]thiazepine-11(10-H)-one. In this synthetic route it is necessary to prepare and purify the compound 2-(2-hydroxyethoxy)ethyl-1-piperazine (HEEP).

Granted European Patent EP 282,236 describes an improved process for the preparation of the compound of formula I which obviates the need to prepare and purify the compound 2-(2-hydroxyethoxy)ethyl)-1-piperazine since this improved process does not use 2-(2-hydroxyethoxy)ethyl-1-piperazine. It also obviates the need to use carboxyethyl piperazine which is used to prepare 2-(2-hydroxyethoxy)ethyl-1-piperazine.

Many Pharmaceuticals are developed as salts of pharmacologically acceptable acids or bases. This is usually done if the biologically active substance itself has a physical form which makes it unsuitable to handle in manufacturing processes. Most manufacturing processes involve materials handling in mixing and formulation which is facilitated by the active materials being either a liquid or free-flowing high melting solids. Although salts can be made with suitable acids or bases these often add nothing to the therapeutic benefit of the pharmaceutical and are therefore redundant biologically. It would be better if the pharmaceutical could be manufactured as the pure active substance.

The reported synthesis of 11-(4-[2-(2-hydroxyethoxy) ethyl]-1-piperazinyl)-dibenzo[b,f][1,4]thiazepine provides 11-(4-[2-(2-hydroxyethoxy)ethyl]-1-piperazinyl)-dibenzo[b,f][1,4]thiazepine as a fumarate salt since it has been necessary to prepare the salt to efficiently obtain a sufficiently pure product. Moreover, to prepare the fumarate salt it has been necessary to first prepare the hydrogen fumarate salt and subsequently convert it to the fumarate.

The present invention is based, at least in part, on an improved method of purifying the compound of formula I, and in particular on a method of purifying the compound of formula I such that the compound of formula I is obtained in a crystalline form.

According to the present invention there is provided crystalline 11-(4-[2-(2-hydroxyethoxy)ethyl]-1-piperazinyl)-dibenzo[b,f][1,4]thiazepine. The crystalline 11-(4-[2-(2-hydroxyethoxy)ethyl]-1-piperazinyl)-dibenzo[b,f][1,4]thiazepine may be converted into one of its pharmaceutically acceptable salts and so the present invention also provides crystalline 11-(4-[2-(2-hydroxyethoxy)ethyl]-1-piperazinyl)-dibenzo[b,f][1,4]thiazepine or a pharmaceutically acceptable salt prepared therefrom.

The crystalline 11-(4-[2-(2-hydroxyethoxy)ethyl]-1-piperazinyl)-dibenzo[b,f][1,4]thiazepine is generally provided in a substantially pure form. It is generally preferred that the crystalline 11-(4-[2-(2-hydroxyethoxy)ethyl]-1-piperazinyl)-dibenzo[b,f][1,4]thiazepine is greater than 90% pure more preferably 99% or greater than 99% pure.

According to the present invention there is also provided a process for preparing crystalline 11-(4-[2-(2-hydroxyethoxy)ethyl]-1-piperazinyl)-dibenzo[b,f][1,4] thiazepine or a pharmaceutically acceptable salt thereof which comprises crystallising 11-(4-[2-(2-hydroxyethoxy) ethyl]-1-piperazinyl)-dibenzo[b,f][1,4]thiazepine from a non-aromatic solvent;
and whereafter, when a pharmaceutically acceptable salt is required, reacting 11-(4-[2-(2-hydroxyethoxy)ethyl]-1-piperazinyl)-dibenzo[b,f][1,4]thiazepine with an acid which affords a pharmaceutically acceptable anion.

According to the present invention there is also provided a process for preparing crystalline 11-(4-[2-(2-hydroxyethoxy)ethyl]-1-piperazinyl)-dibenzo[b,f][1,4] thiazepine or a pharmaceutically acceptable salt thereof which comprises crystallising 11-(4-[2-(2-hydroxyethoxy) ethyl]-1-piperazinyl)-dibenzo[b,f][1,4]thiazepine from a non-aromatic solvent substantially in the absence of water;
and whereafter, when a pharmaceutically acceptable salt is required, reacting 11-(4-[2-(2-hydroxyethoxy)ethyl]-1-piperazinyl)-dibenzo[b,f][1,4]thiazepine with an acid which affords a pharmaceutically acceptable anion.

The crystallisation may be initiated with the aid of a seed crystal.

The salts of 11-(4-[2-(2-hydroxyethoxy)ethyl]-1-piperazinyl)-dibenzo[b,f][1,4]thiazepine will generally comprise acid-addition salts. Convenient salts may be selected from those pharmaceutically acceptable salts known in the art. These may be obtained by any conventional salt preparation method known in the art. For example, salts may be obtained by reacting 11-(4-[2-(2-hydroxyethoxy)ethyl]-1-piperazinyl)-dibenzo[b,f][1,4] thiazepine with a convenient acid, such as, hydrochloric acid maleic acid, fumaric acid, citric acid, phosphonic acid, methanesulphonic acid and sulphuric acid.

Preferred salts include fumarate salts and in particular the hemi-fumarate salt. It is generally preferred that the fumarate salt of 11-(4-[2-(2-hydroxyethoxy)ethyl]-1-piperazinyl)-dibenzo[b,f][1,4]thiazepine is bis-[11-(4-[2-(2-hydroxyethoxy)ethyl]-1-piperazinyl)-dibenzo[b,f][1,4] thiazepine]fumarate.

It is generally preferred, for example, that the solvent is dry. It is further preferred that the 11-(4-[2-(2-hydroxyethoxy)ethyl]-1-piperazinyl)-dibenzo[b,f][1,4] thiazepine is also dry so that the solution formed on dissolving 11-(4-[2-(2-hydroxyethoxy)ethyl]-1-piperazinyl)-dibenzo[b,f][1,4]thiazepine in the solvent is substantially free from water. More especially, the solution formed in the crystallisation process should be free from water.

Thus, in a preferred embodiment there is provided a process for preparing 11-(4-[2-(2-hydroxyethoxy)ethyl]-1-piperazinyl)-dibenzo[b,f][1,4]thiazepine, or a pharmaceutically-acceptable salt thereof, which comprises crystallising 11-(4-[2-(2-hydroxyethoxy)ethyl]-1-piperazinyl)-dibenzo[b,f][1,4]thiazepine from a solution of 11-(4-[2-(2-hydroxyethoxy)ethyl]-1-piperazinyl)-dibenzo[b,f][1,4]thiazepine in a non-aromatic solvent which is free from water. The crystalline 11-(4-[2-(2-hydroxyethoxy)ethyl]-1-piperazinyl)-dibenzo[b,f][1,4]thiazepine may, if desired, be converted to a pharmaceutically-acceptable salt, as mentioned above.

Examples of suitable solvents include, for example, esters such as those of formula $R^1CO_2R^2$ wherein $R^1$ and $R^2$ are alkyl groups; ethers of formula $R^3OR^4$ wherein $R^3$ and $R^4$ are alkyl groups; and ketones of formula $R^5COR^6$ wherein $R^5$ and $R^6$ are alkyl groups.

Particular values of $R^1$, $R^2$, $R^3$, $R^4$, $R^5$ and $R^6$ include, for example, (1–6C)alkyl such as methyl, ethyl, n-propyl, iso-propyl, n-butyl, iso-butyl, sec-butyl, tert-butyl, pentyl and hexyl. Conveniently, $R^1$, $R^2$, $R^3$ and $R^4$ are selected from (1–4C)alkyl.

Specific examples of suitable solvents includes for example, ethyl acetate, isobutyl acetate, methyl iso-butylketone and methyl tert-butyl ether.

Solvents of particular interest include, for example, ethers. Thus, a solvent of particular interest is methyl tert-butyl ether.

The temperature of the solution containing 11-(4-[2-(2-hydroxyethoxy)ethyl]-1-piperazinyl)-dibenzo[b,f][1,4]thiazepine may be decreased during the crystallisation. In general, the temperature will be decreased to about 0° C. Conveniently, the temperature is decreased gradually over a period of time. Thus, in a specific example, the temperature is decreased to ambient temperature (about 25° C.) and then further decreased to about 0° C. over a period greater than 1 hour and generally greater than 2 hours. In particular, the temperature is decreased from ambient temperature to 0° C. over a period of about 2 to 4 hours, preferably about 3 hours. Where a seed crystal is used it will generally be added to the crystallisation mixture when that mixture is at ambient temperature. In the case where the temperature is decreased, the seed crystal will, in general, be added just before the temperature is decreased (from ambient temperature).

The quantity of solvent employed to crystallise 11-(4-[2-(2-hydroxyethoxy)ethyl]-1-piperazinyl)-dibenzo[b,f][1,4]thiazepine will vary according to the precise solvent selected. In particular the quantity of solvent is that which, when 11-(4-[2-(2-hydroxyethoxy)ethyl]-1-piperazinyl)-dibenzo[b,f][1,4]thiazepine is dissolved in it gives a concentration (before crystallisation) of about 120 to 160 mg/ml, more particularly 130 to 150 mg/ml. It is generally preferred that the quantity of solvent is that which gives a concentration (before crystallisation) of about 135 to 145 mg/ml.

In a particular embodiment of the present invention there is provided a method of purifying 11-(4-[2-(2-hydroxyethoxy)ethyl]-1-piperazinyl)-dibenzo[b,f][1,4]thiazepine comprising crystallising 11-(4-[2-(2-hydroxyethoxy)ethyl]-1-piperazinyl)-dibenzo[b,f][1,4]thiazepine from methyl tert-butylether in the absence of water.

Preferred, particular and specific conditions include those mentioned above.

As mentioned above, the crystalline product may, if desired, be converted to a pharmaceutically acceptable salt.

In a further embodiment of the present invention there is provided a method of preparing the fumarate salt of 11-(4-[2-(2-hydroxyethoxy)ethyl]-1-piperazinyl)-dibenzo[b,f][1,4]thiazepine, which method comprises reacting crystalline 11-(4-[2-(2-hydroxyethoxy)ethyl]-1-piperazinyl)-dibenzo[b,f][1,4]thiazepine with fumaric acid.

The crystalline 11-(4-[2-(2-hydroxyethoxy)ethyl]-1-piperazinyl)-dibenzo[b,f][1,4]thiazepine will generally be prepared as herein before defined.

Crystalline 11-(4-[2-(2-hydroxyethoxy)ethyl]-1-piperazinyl)-dibenzo[b,f][1,4]thiazepine will generally be reacted with the fumaric acid in a solvent such as an alcohol. Examples of suitable alcohols will include methanol and ethanol. A particularly suitable solvent is ethanol which may conveniently be in the form of industrial methylated spirits (IMS).

The present invention also provides a method of preparing crystalline 11-(4-[2-(2-hydroxyethoxy)ethyl]-1-piperazinyl)-dibenzo[b,f][1,4]thiazepine, or a pharmaceutically acceptable salt thereof, from a solution of 11-(4-[2-(2-hydroxyethoxy)ethyl]-1-piperazinyl)-dibenzo[b,f][1,4]thiazepine in an aromatic solvent which process comprises:

a) adding water and an acid to the solution of 11-(4-[2-(2-hydroxyethoxy)ethyl]-1-piperazinyl)-dibenzo[b,f][1,4]thiazepine in the aromatic solvent;

b) separating the aqueous and organic phases;

c) adding a non-aromatic solvent and a base to the aqueous phase;

d) separating the aqueous and the non-aromatic solvent phases;

e) drying the non-aromatic solvent phase;

f) crystallising 11-(4-[2-(2-hydroxyethoxy)ethyl]-1-piperazinyl)-dibenzo[b,f][1,4]thiazepine from the non-aromatic solvent; and whereafter, if a pharmaceutically acceptable salt is desired reacting the 11-(4-[2-(2-hydroxyethoxy)ethyl]-1-piperazinyl)-dibenzo[b,f][1,4]thiazepine with an acid which affords a pharmaceutically acceptable anion.

Particular, preferred and specific values include the values mentioned above.

The aromatic solvent is preferably toluene.

It will be appreciated that the amount/strength of acid added in step (a) will be such that the aqueous phase is made acidic and the amount/strength of base added in step ((c) will be such that the aqueous phase is made basic.

The compound of this invention is a central nervous system depressant and may be used as a tranquilizer for the relief of hyperactivity states, for example, in mice, cats, rats, dogs and other mammalian species, and additionally for the management of psychotic states in man, in the same manner as chlorpromazine. For this purpose the 11-(4-[2-(2-hydroxyethoxy)ethyl]-1-piperazinyl)-dibenzo[b,f][1,4]thiazepine, or physiologically acceptable acid addition salt thereof, may be administered orally or parenterally in a conventional dosage form such as tablets, pill, capsule, injectable or the like. The dosage in mg/kg of body weight of a compound of the present invention in mammals will vary according to the size of the animal and particularly with respect to the brain/body weight ratio. In general, a higher mg/kg dosage for a small animal such as a dog will have the same effect as a lower mg/kg dosage in an adult human. A minimum effective dosage for the compound of formula I will be at least about 1.0 mg/kg of body weight per day for mammals with a maximum dosage for a small mammal such as a dog, of about 200 mg/kg per day. For humans, a dosage of about 1.0 to 40 mg/kg per day will be effective, for example, about 50 to 2000 mg/day for an average person weighing 50 kg. The dosage can be given once daily or in divided doses, for example, 2 to 4 doses daily. The dose may be conventionally formulated in an oral or parenteral dosage form by compounding about 25 to 500 mg per unit of dosage of conventional vehicle, excipient, binder, preservative, stabilizer, flavor or the like as called for by accepted pharmaceutical practice, for example, as described in U.S. Pat. No. 3,755,340. The compound of formula I (or salt) may be used in pharmaceutical compositions as previously described or be contained in or co-administered with one or more known drugs.

Thus, according to the present invention there is also provided a pharmaceutical composition comprising crystalline 11-(4-[2-(2-hydroxyethoxy)ethyl]-1-piperazinyl)-dibenzo[b,f][1,4]thiazepine, or a pharmaceutically acceptable salt prepared therefrom, together with a pharmaceutically acceptable diluent or carrier.

In particular, there is provided a pharmaceutical composition comprising crystalline 11-(4-[2-(2-hydroxyethoxy) ethyl]-1-piperazinyl)-dibenzo[b,f][1,4]thiazepine and a pharmaceutically acceptable diluent or carrier.

The present invention also provides a method of treating neuropsychiatric disorders (in particular, a method of treating psychoses, more particularly schizophrenia) using crystalline 11-(4-[2-(2-hydroxyethoxy)ethyl]-1-piperazinyl)-dibenzo[b,f][1,4]thiazepine or a pharmaceutically acceptable salt prepared therefrom.

In particular, the present invention provides a method of treating neuropsychiatric disorders, comprising administering an effective amount of crystalline 11-(4-[2-(2-hydroxyethoxy)ethyl]-1-piperazinyl)-dibenzo[b,f][1,4] thiazepine to a warm-blooded mammal such as man. In particular, the present invention provides a method of treating psychoses, more particularly schizophrenia.

The present invention also provides the use of crystalline 11-(4-[2-(2-hydroxyethoxy)ethyl]-1-piperazinyl)-dibenzo[b,f][1,4]thiazepine in the manufacture of a medicament for treating neuropsychiatric disorders and in particular psychoses such as schizophrenia.

As mentioned above, the present invention offers advantages over known methods of preparing 11-(4-[2-(2-hydroxyethoxy)ethyl]-1-piperazinyl)-dibenzo[b,f][1,4] thiazepine and salts.

Firstly, the present invention provides crystalline 11-(4-[2-(2-hydroxyethoxy)ethyl]-1-piperazinyl)-dibenzo[b,f][1,4]thiazepine. In particular the invention provides processes for the preparation crystalline 11-(4-[2-(2-hydroxyethoxy) ethyl]-1-piperazinyl)-dibenzo[b,f][1,4]thiazepine which is of high purity. In general, the crystalline material had a high melting point consistent with a crystalline solid of high purity and good quality.

Previously, pure 11-(4-[2-(2-hydroxyethoxy)ethyl]-1-piperazinyl)-dibenzo[b,f][1,4]thiazepine has been obtained by provision of a purified salt, the fumarate. This has necessitated preparation of the hydrogen fumarate salt followed by subsequent conversion to the fumarate salt. This conversion is a relatively low output process which requires the use of relatively dilute reaction mixtures to ensure the formation of the desired fumarate salt rather than a mixture of hydrogen fumarate and fumarate salt forms.

By utilising purified crystalline 11-(4-[2-(2-hydroxyethoxy)ethyl]-1-piperazinyl)-dibenzo[b,f][1,4] thiazepine, the fumarate salt may be prepared in a relatively high output process since the difficulties associated with obtaining the correct salt form are minimised.

The present invention also provides processes for the preparation of 11-(4-[2-(2-hydroxyethoxy)ethyl]-1-piperazinyl)-dibenzo[b,f][1,4]thiazepine and its salts in a more productive manner than previously reported which uses plant and/or materials such as solvents more efficiently.

The invention will now be illustrated by the following non-limiting examples in which, unless stated otherwise:
(i) temperature are given in degrees Celsius (C): operations were carried out at room or ambient temperature that is, at a temperature in the range of 18–25° C.
(ii) evaporation of solvent was carried out using a rotary evaporator under reduced pressure (600–4000 pascals; 4.5–30 mmHg) with a bath temperature of up to 60° C.;
(iii) in general the course of reactions was followed by TLC and/or HPLC and reaction times are given for illustration only;
(iv) melting points are uncorrected and (dec) indicates decomposition; the melting points given are those obtained for the materials prepared as described: polymorphism may result in isolation of materials with different melting points in some preparations;
(v) all final products were essentially pure by TLC and/or HPLC and had satisfactory nuclear magnetic resonance (NMR) spectra and microanalytical data;
(vi) yields are given for illustration only;
(vii) reduced pressures are given as absolute pressures in pascals (Pa); other pressures are given as gauge pressures in bars;
(viii) chemical symbols have their usual meanings, the following abbreviations have also been used: v(volume), w(weight), mp (melting point), L (liters), ml (milliliters), g (grams), mmol (millimoles), mg (milligrams), min (minutes), h (hours), IMS (industrial methylated spirits); and The 11-(4-[2-(2-hydroxyethoxy)ethyl]-1-piperazinyl)-dibenzo[b,f][1,4]thiazepine was prepared as described in granted European Patent No. EP 282,236. This compound may also be prepared as described in granted European Patent No. 240,228.

EXAMPLE 1

(a) Water (106 ml) was added to a stirred mixture of 11-(4-[2-(2-hydroxyethoxy)ethyl]-1-piperazinyl)-dibenzo[b,f][1,4]thiazepine (59 g) in toluene at 40° C. Concentrated hydrochloric acid (21.4 ml) was added to the mixture and the mixture was stirred vigorously for 15 minutes at 40° C. The phases were separated.

Methyl tert-butyl ether (256 ml) was added to the aqueous phase. Aqueous sodium hydroxide solution (15.4 ml, density 1.5 g/cm$^3$) was added and the mixture was warmed to 45° C. and stirred vigorously for 15 minutes. The mixture was allowed to settle and the phases were separated. The organic phase was washed with water (2×25 ml) at 45° C. and then dried by distillation at 55° C. using a Dean and Stark separator. The dried mixture was allowed to cool to 25° C. seeded and stirred overnight to give a solid. The mixture was cooled to 0° C. and maintained at 0° C. for 4 hours. The solid was collected by filtration, washed with methyl tert-butyl ether and dried in a vacuum oven at 50° C. overnight.

There was thus obtained 11-(4-[2-(2-hydroxyethoxy) ethyl]-1-piperazinyl)-dibenzo[b,f][1,4]thiazepine (46.7 g) as a white crystalline solid, m.p. 82–84° C.

(b) IMS (35 ml) was added to free base (30.0 g) and the stirred mixture was heated at 60° C. in a 100 ml flask to give a solution. This solution was transferred to a 500 ml reactor vessel via a sinter. The 100 ml flask was washed with warm (60° C.) IMS (10 ml) and the washings added to the reactor vessel. The mixture in the reactor vessel was warmed to 60° C. with stirring.

Fumaric acid (4.65 g) and IMS (60 ml) were added to the 100 ml flask. The mixture was heated to 60° C. with stirring to give a solution which contained a small number of solid lumps of material. The mixture was added to the reaction vessel via the sinter so as to filter the mixture and remove the lumps. The resulting mixture in the reaction vessel was stirred to give crystalline material.

IMS (10 ml) was added to the 100 ml flask, warmed to 60° C. and transferred to the reaction vessel. The thick crystalline mass in the reaction vessel was heated to reflux and then allowed to cool to ambient temperature, to give a solid. The stirred mixture was cooled to 0° C. and the temperature of the mixture maintained at this temperature for 1 hour. The solid was collected by filtration and washed with cool (0 to 5° C.) IMS (30 ml). This IMS had been used to wash the reaction vessel out. The solid was dried in a vacuum oven at 55° C. overnight to give bis-[11-(4-[2-(2-hydroxyethoxy)ethyl]-1-piperazinyl)-dibenzo[b,f][1,4]thiazepine]fumarate as a white crystalline solid (32.7 g); 94.4% yield).

EXAMPLE 2

Using a similar method to that described in Example 1, 11-(4-[2-(2-hydroxyethoxy)ethyl]-1-piperazinyl)-dibenzo[b,f][1,4]thiazepine was crystallised from the solvents listed below in place of methyl tert-butylether.

| Solvent | Strength (%) | Yield (%) | M.P. (° C.) |
|---|---|---|---|
| Ethyl acetate[1] | 100 | 39.7 | —[2] |
| Iso-butyl acetate | 97.5 | 70.1 | 83–86 |
| Methyl iso-butylketone | 99.4 | 69.7 | 83–86 |
| Methyl iso-butylketone[3] | 99.3 | 67.8 | 83–86 |
| Methyl tert-butylether | 100 | 86 | 83–86 |
| Methyl tert-butylether | 99 | 81 | 83–86 |

[1]crystallised from previously isolated 11-(4-[2-(2-hydroxyethoxy)ethyl]-1-piperazinyl)-dibenzo[b,f][1,4]thiazepine
[2]good solid
[3]80% charge Strength is a measure of purity. The % strength is the % of desired ingredient, 11-(4-[2-(2-hydroxyethoxy)ethyl]-1-piperazinyl)-dibenzo[b,f][1,4]thiazepine, in the weight of material isolated.

EXAMPLE 3

The following illustrate representative pharmaceutical dosage forms containing a compound of 11-(4-[2-(2-hydroxyethoxy)ethyl]-1-piperazinyl)-dibenzo[b,f][1,4]thiazepine and salts thereof, for example as illustrated in any of the previous Examples, (hereafter referred to as "compound X"), for therapeutic or prophylactic use in humans:

| | mg/tablet |
|---|---|
| (a) Tablet | |
| Compound X | 50.0 |
| Mannitol, USP | 223.75 |
| Croscarmellose sodium | 6.0 |
| Maize starch | 15.0 |
| Hydroxypropylmethylcellulose (HPMC), | 2.25 |
| Magnesium stearate | 3.0 |
| (b) Capsule | |
| Compound X | 10.0 |
| Mannitol, USP | 488.5 |

-continued

| | mg/tablet |
|---|---|
| Croscarmellose sodium | 15.0 |
| Magnesium stearate | 1.5 |

The above formulations may be obtained by conventional procedures well known in the pharmaceutical art. The tablets may be enteric coated by conventional means for example to provide a coating of cellulose acetate phthalate.

What is claimed is:

1. A compound which is crystalline 11-(4-[2-(2-hydroxyethoxy)ethyl]-1-piperazinyl)-dibenzo[b,f][1,4]thiazepine.

2. A compound as claimed in claim 1 in which the crystalline 11-(4-[2-(2-hydroxyethoxy)ethyl]-1-piperazinyl)-dibenzo[b,f][1,4]thiazepine is greater than 90% pure.

3. A compound as claimed in claim 2 wherein the crystalline 11-(4-[2-(2-hydroxyethoxy)ethyl]-1-piperazinyl)-dibenzo[b,f][1,4]thiazepine is greater than 99% pure.

4. A process for preparing crystalline 11-(4-[2-(2-hydroxyethoxy)ethyl]-1-piperazinyl)-dibenzo[b,f][1,4]thiazepine, or a pharmaceutically acceptable salt thereof, which comprises crystallising 11-(4-[2-(2-hydroxyethoxy)ethyl]-1-piperazinyl)-dibenzo[b,f][1,4]thiazepine from a non-aromatic solvent;

and optionally thereafter forming a salt by reacting the 11-(4-[2-(2-hydroxyethoxy)ethyl]-1-piperazinyl)-dibenzo[b,f][1,4]thiazepine with an acid which affords a pharmaceutically acceptable anion.

5. A process for preparing 11-(4-[2-(2-hydroxyethoxy)ethyl]-1-piperazinyl)-dibenzo[b,f][1,4]thiazepine, or a pharmaceutically-acceptable salt thereof, which comprises crystallising 11-(4-[2-(2-hydroxyethoxy)ethyl]-1-piperazinyl)-dibenzo[b,f][1,4]thiazepine from a solution of 11-(4-[2-(2-hydroxyethoxy)ethyl]-1-piperazinyl)-dibenzo[b,f][1,4]thiazepine in a non-aromatic solvent and in which the solution is substantially free from water;

and optionally thereafter forming a salt by reacting the 11-(4-[2-(2-hydroxyethoxy)ethyl]-1-piperazinyl)-dibenzo[b,f][1,4]thiazepine with an acid which affords a pharmaceutically acceptable anion.

6. A process as claimed in any one of claims 4 and 5 wherein the non-aromatic solvent is selected from an ester of formula $R^1CO_2R^2$ wherein $R^1$ and $R^2$ are alkyl groups; an ether of formula $R^3OR^4$ wherein $R^3$ and $R^4$ are alkyl groups; and a ketone of formula $R^5COR^6$ wherein $R^5$ and $R^6$ are alkyl groups.

7. A process as claimed in claim 6 wherein $R^1$, $R^2$, $R^3$ and $R^4$ are selected from (1–4C)alkyl.

8. A process as claimed in claim 6 wherein the non-aromatic solvent is selected from ethyl acetate, isobutyl acetate, methyl iso-butylketone and methyl tert-butyl ether.

9. A process as claimed in any one of claims 4 and 5 wherein the solvent is selected from methyl tert-butyl ether.

10. A process of purifying 11-(4-[2-(2-hydroxyethoxy)ethyl]-1-piperazinyl)-dibenzo[b,f][1,4]thiazepine comprising crystallising 11-(4-[2-(2-hydroxyethoxy)ethyl]-1-piperazinyl)-dibenzo[b,f][1,4]thiazepine from methyl tert-butylether in the absence of water.

11. A process as claimed in any one of claims 4, 5 and 10 wherein the 11-(4-[2-(2-hydroxyethoxy)ethyl]-1-piperazinyl)-dibenzo[b,f][1,4]thiazepine and the non-aromatic solvent are heated to give a solution and the temperature of the solution containing the 11-(4-[2-(2-hydroxyethoxy)ethyl]-1-piperazinyl)-dibenzo[b,f][1,4]

thiazepine is decreased to ambient temperature and then further decreased to about 0° C. over a period greater than 1 hour.

12. A process as claimed in claim 11 wherein the temperature is decreased from ambient temperature to 0° C. over a period of about 2 to 4 hours.

13. A process as claimed in claim 11 wherein the temperature is decreased from ambient temperature to 0° C. over a period of about 3 hours.

14. A process as claimed in any one of claims 4, 5 and 10 wherein the quantity of the non-aromatic solvent is that which, when 11-(4-[2-(2-hydroxyethoxy)ethyl]-1-piperazinyl)-dibenzo[b,f][1,4]thiazepine is dissolved in it, gives a concentration (before crystallisation) of about 120 to 160 mg/ml.

15. A process as claimed in claim 14 wherein the quantity of non-aromatic solvent gives a concentration (before crystallisation) of 135 to 145 mg/ml.

16. A process as claimed in any one of claims 4, 5 and 10, which comprises reacting crystalline 11-(4-[2-(2-hydroxyethoxy)ethyl]-1-piperazinyl)-dibenzo[b,f][1,4]thiazepine with fumaric acid to give the fumarate salt of 11-(4-[2-(2-hydroxyethoxy)ethyl]-1-piperazinyl)-dibenzo[b,f][1,4]thiazepine.

17. A process for preparing crystalline 11-(4-[2-(2-hydroxyethoxy)ethyl]-1-piperazinyl)-dibenzo[b,f][1,4]thiazepine, or a pharmaceutically acceptable salt thereof, from a solution of 11-(4-[2-(2-hydroxyethoxy)ethyl]-1-piperazinyl)-dibenzo[b,f][1,4]thiazepine in an aromatic solvent, which process comprises:

a) adding water and an acid to the solution of 11-(4-[2-(2-hydroxyethoxy)ethyl]-1-piperazinyl)-dibenzo[b,f][1,4]thiazepine in the aromatic solvent, which process comprises:

b) separating the aqueous and organic phases;

c) adding a non-aromatic solvent and a base to the aqueous phase;

d) separating the aqueous and the non-aromatic solvent phases;

e) drying the non-aromatic solvent phase;

f) crystallising 11-(4-[2-(2-hydroxyethoxy)ethyl]-1-piperazinyl)-dibenzo[b,f][1,4]thiazepine from the non-aromatic solvent; and optionally thereafter forming a salt by reacting the 11-(4-[2-(2-hydroxyethoxy)ethyl]-1-piperazinyl)-dibenzo[b,f][1,4]thiazepine with an acid which affords a pharmaceutically acceptable anion.

18. A process as claimed in claim 17 wherein the aromatic solvent is toluene.

19. A process as claimed in claim 17 wherein step (f) is carried out as claimed in any one of claims 4, 5 and 10.

20. A pharmaceutical composition comprising crystalline 11-(4-[2-(2-hydroxyethoxy)ethyl]-1-piperazinyl)-dibenzo[b,f][1,4]thiazepine and a pharmaceutically acceptable diluent or carrier.

21. A method for the treatment of neuropsychiatric disorders in a warm-blooded animal in need thereof comprising administering to such animal a neuropsychiatric treatment effective amount of crystalline 11-(4-[2-(2-hydroxyethoxy)ethyl]-1-piperazinyl)-dibenzo[b,f][1,4]thiazepine.

22. A method for the treatment of psychoses in a warm-blooded animal in need thereof comprising administering to such animal a psychoses treatment effective amount of crystalline 11-(4-[2-(2-hydroxyethoxy)ethyl]-1-piperazinyl)-dibenzo[b,f][1,4]thiazepine.

* * * * *